US00PP17212P2

(12) United States Plant Patent
Gossett

(10) Patent No.: US PP17,212 P2
(45) Date of Patent: Nov. 14, 2006

(54) ***SEDUM* PLANT NAMED 'HOT STUFF'**

(50) Latin Name: *Sedum spectabile*
Varietal Denomination: Hot Stuff

(75) Inventor: Gary J. Gossett, Portland, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 16 days.

(21) Appl. No.: 11/152,488

(22) Filed: Jun. 13, 2005

(51) Int. Cl.
*A01H 5/00* (2006.01)

(52) U.S. Cl. ..... Plt./263

(58) Field of Classification Search ..... Plt./263
See application file for complete search history.

(56) References Cited

PUBLICATIONS http://www.terranovanurseries.com/wholesale/modules.ph-p?name=Content&pa=showpage&... "*Sedum spectabile* 'Hot Stuff' PPAF PVR" Apr. 11, 2006.*

* cited by examiner

*Primary Examiner*—Wendy Haas
(74) *Attorney, Agent, or Firm*—Klarquist Sparkman, LLP

(57) ABSTRACT

A new and distinct *Sedum spectabile* plant characterized by an extremely compact habit with stems that do not fall over after bloom and large purple red flower heads.

1 Drawing Sheet

Botanical classification: *Sedum spectabile.*
Variety denomination: 'Hot Stuff'.

The present invention relates to a new and distinct cultivar of *Sedum spectabile* and given the cultivar name of 'Hot Stuff'. *Sedum* is in the family Crassulaceae. *Sedum* 'Hot Stuff' originated as a seedling from an open pollinated *Sedum spectabile* 'Brilliant' (unpatented).

This new and unique *Sedum* is distinguished by:

1. Large purple red flower heads.
2. Short stature with strong upright stems.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The drawing shows a two year old *Sedum* 'Hot Stuff' growing in the field in September in Canby, Oreg.

DETAILED PLANT DESCRIPTION

Figure 1:
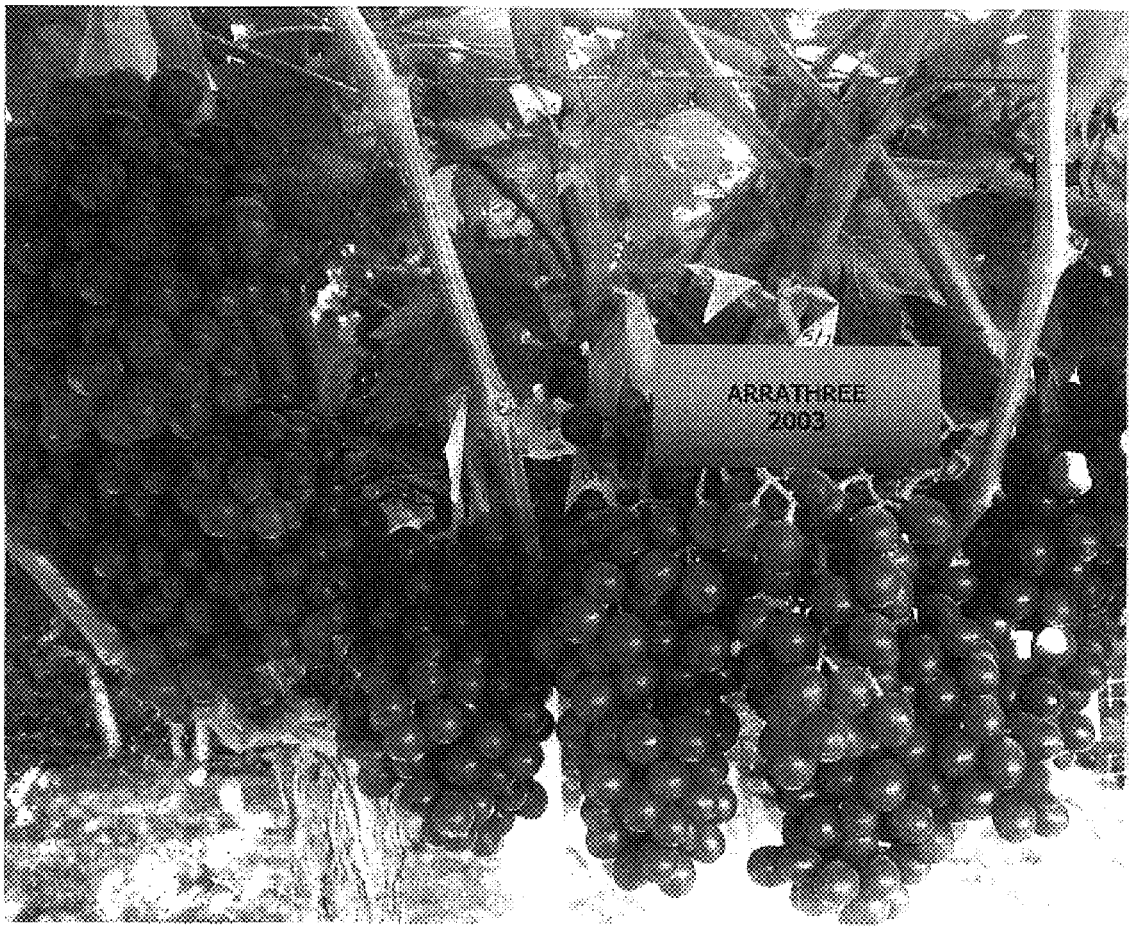

The following is a detailed description of the new *Sedum* based on observations of a two year old specimen grown in the ground in full sun under typical outdoor conditions in the trial fields in Canby, Oreg. Canby is Zone 8 on the USDA Hardiness map. Temperatures range from a high of 95 degrees F. in August to 32 degrees F. in January. Normal rainfall in Canby is 42.8 inches per year. The color descriptions are all based on The Royal Horticultural Society Colour Chart.

Botanical classification: *Sedum spectabile.*
Variety denomination: 'Hot Stuff'.

Plant:

*Type.*—Herbaceous perennial.
*Hardiness.*—USDA Zone 4 to 9.
*Size.*—35 cm tall from the ground to the top of the foliage and 38 cm wide.
*Habit.*—Clump forming.
*Vigor.*—Excellent.
*Root description.*—Multiple fleshy roots from each crown, Yellow White 158A, grows to 5 mm wide and 20 cm long in clay loam soil.

Stem:

*Height.*—20 cm, unbranched.
*Width.*—9 mm.
*Color.*—Yellow Green 146C.
*Texture.*—Succulent.
*Surface.*—Glaucous.

Leaf:

*Type.*—Simple, cauline, succulent.
*Arrangement.*—Opposite.
*Shape.*—Broadly obovate.
*Venation.*—Pinnate.
*Margins.*—Shallowly and irregularly serrate.
*Apex.*—Broadly acute.
*Base.*—Cuneate.
*Blade size.*—7.5 cm long and 4 cm wide.
*Surface.*—Glaucous.
*Shininess.*—Matte.
*Texture.*—Thick, spongy, succulent.
*Petiole.*—Leaves sessile.
*Leaf color.*—Topside — Blue Green (closest to Green138A). Bottom side — Blue Green (closest to Green 138B).

Inflorescence:

*Type.*—Terminal, flat topped, 5-branched dense corymbose cyme.

*Number of flowers.*—100 to 250 per stem.
*Size.*—10 to 13 cm wide and 10 cm wide.
*Peduncle.*—Height from top of true leaves — 11.5 cm. Diameter — 6 mm. Color — Yellow Green 146D. Texture — Succulent. Surface — Glaucous.
*Pedicel.*—Variable in size from 7 to 10 mm, Yellow Green 146D, glaucous.
*Bloom period.*—September through October in Canby, Oreg.

Flower bud:
*Size.*—2 mm wide, 6 mm deep.
*Description.*—Ovoid.
*Color.*—Red Purple 70C.

Flower:
*Type.*—Complete, actinomorphic.
*Shape.*—Stellate.
*Size.*—0.9 cm deep and 1.1 cm wide.
*Petal count.*—5.
*Petal color.*—Purple red, Red Purple 70A to B.
*Petal shape.*—Lanceolate with acute tips.
*Petal size.*—7 mm long, 1.8 mm wide.
*Calyx.*—Divided ⅘ to the base, campanulate, 3 mm deep and wide.
*Calyx color.*—Yellow Green 149C.
*Sepal number.*—5 lobes.
*Stamen number.*—5.
*Carpel.*—Prominent, 4 separate.
*Pistil size.*—6 mm deep and 1 mm wide.
*Pistil color.*—Red Purple 67A.
*Stamens.*—8, Red Purple 70B.
*Filaments.*—7 to 9 mm long.
*Pollen color.*—Purple Black, Greyed Purple 187A.
*Fragrance.*—None.
*Lastingness.*—Each inflorescence lasts 1 month.

Fruit:
*Type.*—Ventrally dehiscent follicle, erect, attenuate.
*Fertility.*—Good.
*Color.*—Brown 200A.

Seed:
*Shape.*—Narrowly oval, somewhat winged.
*Size.*—0.6 mm long.
*Color.*—Brown 200A.

Disease and pest resistance: *Sedum* are susceptible to root rots, scale and mealy bugs. No special resistance has been noted.

COMPARISON TO SIMILAR *SEDUM*

Compared to the seed parent, *Sedum spectabile* 'Brilliant', an unpatented plant, *Sedum* 'Hot Stuff' is shorter with brighter flowers. Stems of the new variety do not fall over after bloom.

Compared to *Sedum spectabile* 'Meteor', an unpatented plant, *Sedum* 'Hot Stuff' is shorter with red purple rather than dark red purple flowers. Stems of the new variety do not fall over after bloom.

I claim:

1. A new and distinct hybrid of *Sedum* plant as herein illustrated and described.

* * * * *